United States Patent [19]
Patterson et al.

[11] 4,352,636
[45] Oct. 5, 1982

[54] DUAL PISTON PUMP

[75] Inventors: Williams G. Patterson, Palo Alto; Allen B. Rochkind, Santa Cruz; Leslie A. Miller, San Jose; Martin P. T. Bradley, Cupertino, all of Calif.

[73] Assignee: Spectra-Physics, Inc., San Jose, Calif.

[21] Appl. No.: 139,648

[22] Filed: Apr. 14, 1980

[51] Int. Cl.³ ............................................. F04B 49/06
[52] U.S. Cl. ...................................... 417/22; 417/42; 417/45; 417/53; 417/265
[58] Field of Search ................... 417/265, 22, 42, 45, 417/244, 53, 18, 20, 43

[56] References Cited

U.S. PATENT DOCUMENTS

| | | | |
|---|---|---|---|
| 3,597,114 | 8/1971 | Hrdina | 417/215 |
| 3,847,507 | 11/1974 | Sakiyama et al. | 417/42 X |
| 4,067,666 | 1/1978 | Richards | 417/265 |
| 4,128,476 | 12/1978 | Rock | 210/101 X |
| 4,137,011 | 1/1979 | Rock | 417/42 X |
| 4,180,375 | 12/1979 | Magnussen | 417/45 X |
| 4,245,963 | 1/1981 | Hutchins et al. | 417/265 |

*Primary Examiner*—Carlton R. Croyle
*Assistant Examiner*—Edward Look
*Attorney, Agent, or Firm*—Donald C. Feix

[57] ABSTRACT

A pump for producing a substantially smooth and continuous outflow of liquid at relatively high pressure has two piston assemblies flow connected in series. The first piston assembly includes a pressure piston having a long suction stroke and a relatively short and abrupt expulsion stroke. A valve at the inlet of the pressurization piston allows flow to enter (but not exit), and a valve at the outlet of the pressurization piston allows flow to exit (but not enter). The second piston assembly includes a damper piston which functions as a mechanically driven damper to smooth the outflow from the pressure piston. This smoothing is accomplished by storing of the liquid displaced by the expulsion stroke of the pressure piston and then delivering the stored pressurized liquid to the pump outlet during the suction stroke of the pressure piston.

The drive for the pistons is constructed to produce an increased outflow of pressurized liquid for a short interval at the beginning of the expulsion stroke of the pressure piston to compensate for compressibility of the liquid at high pressure. At low pressure, the stepper motor drive is slowed down in response to the sensing of the increase of the outflow during this short interval to maintain the outflow smooth and continuous during this part of the cycle of operation.

23 Claims, 18 Drawing Figures

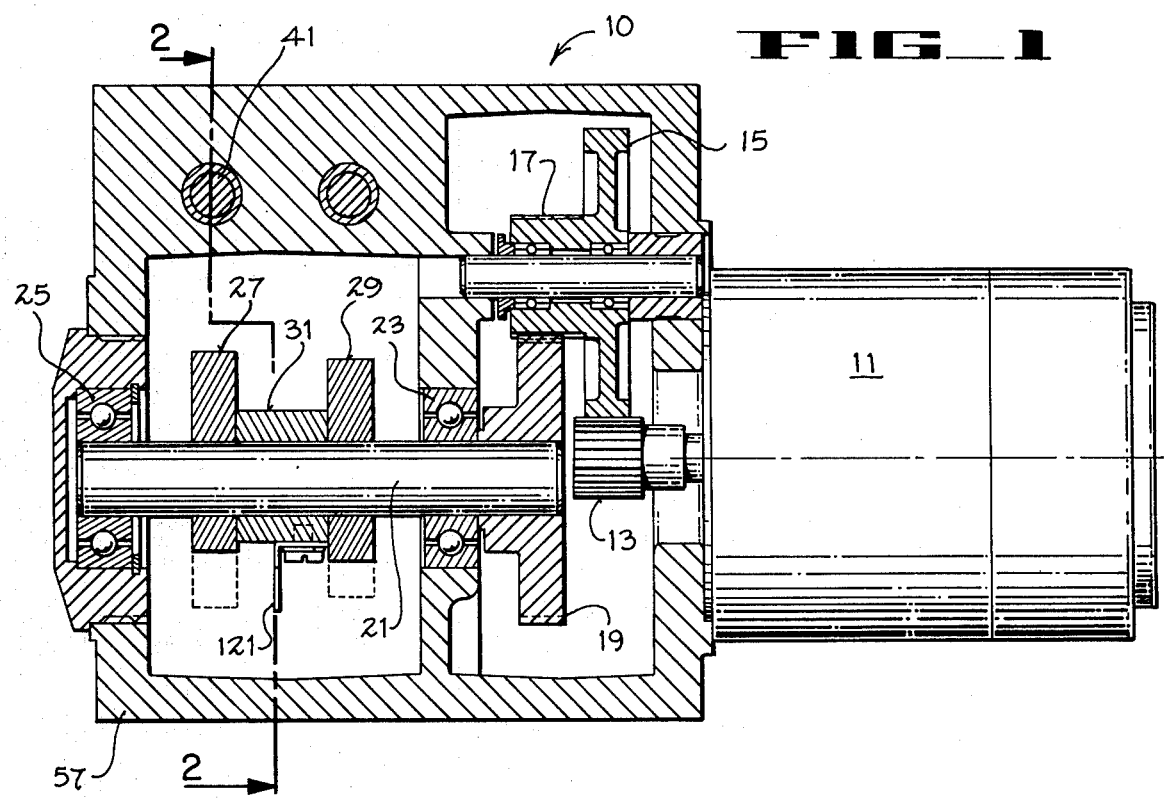
FIG_1
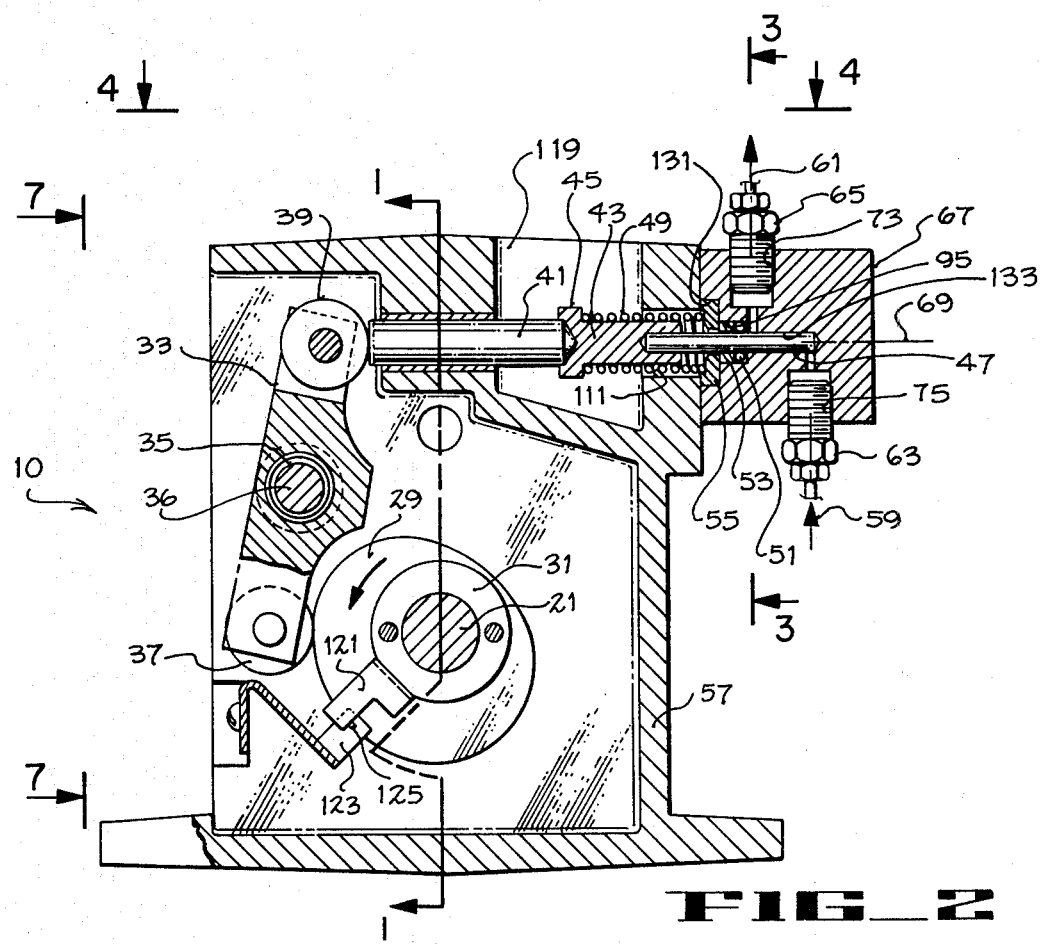
FIG_2

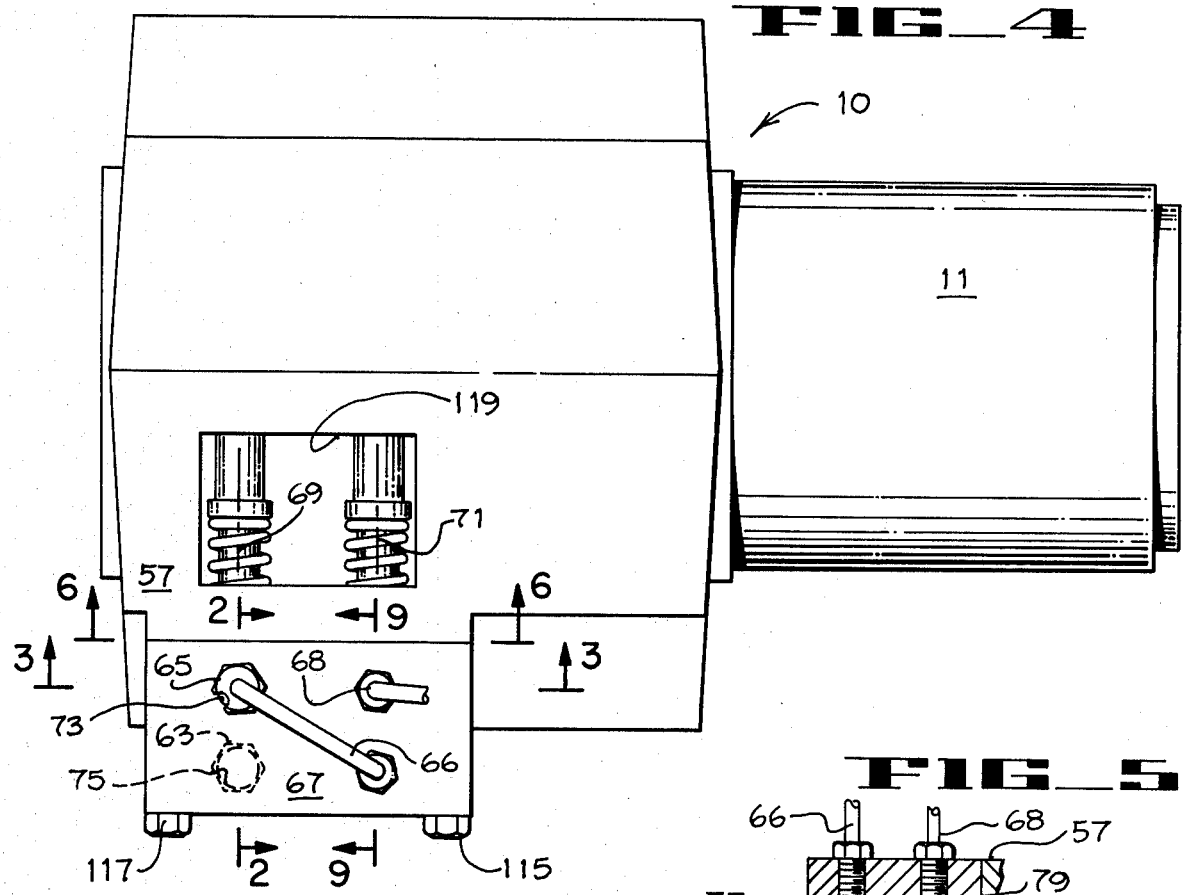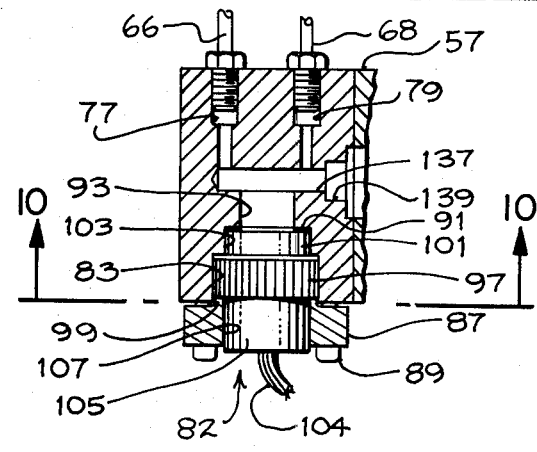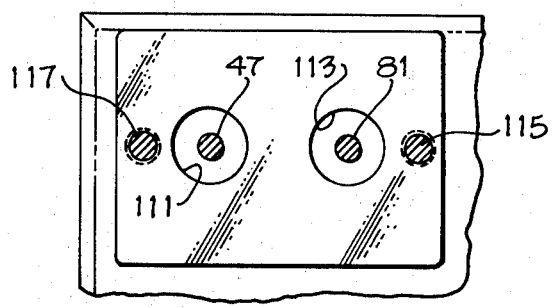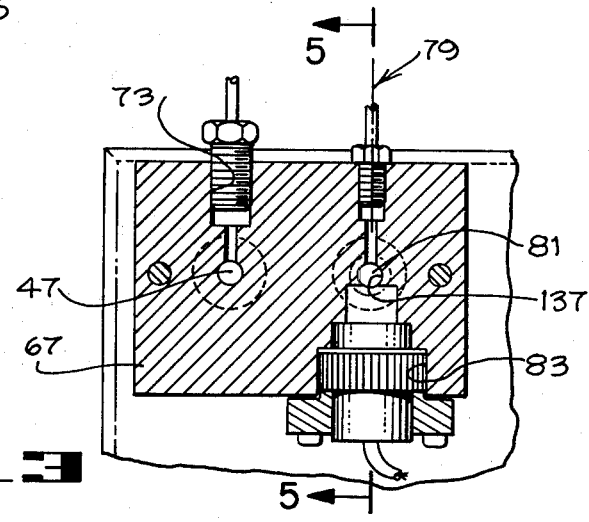

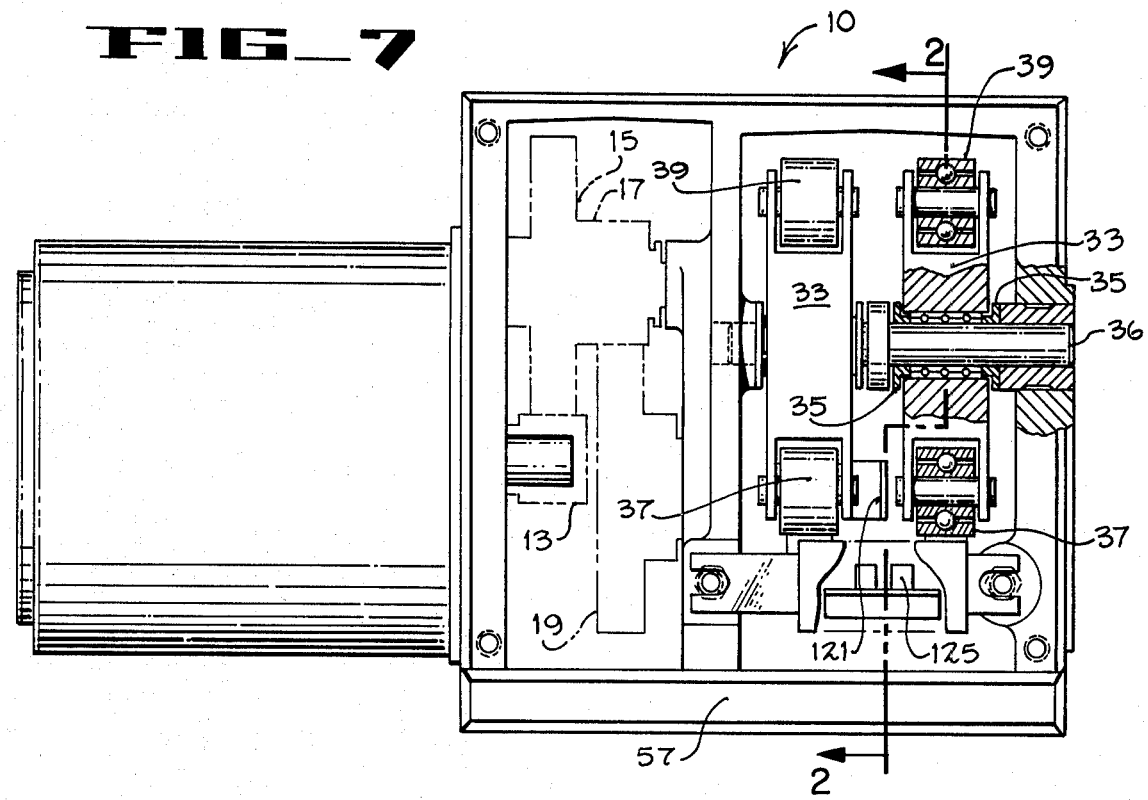
FIG_7
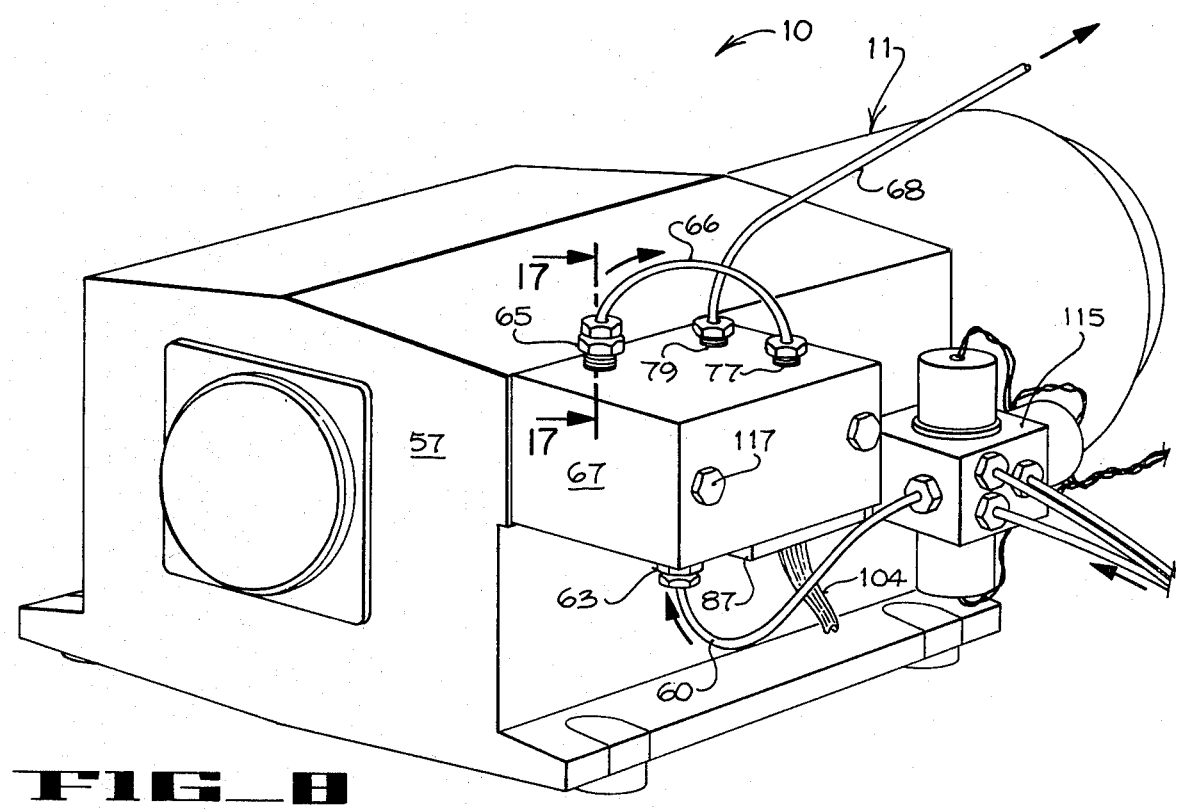
FIG_8

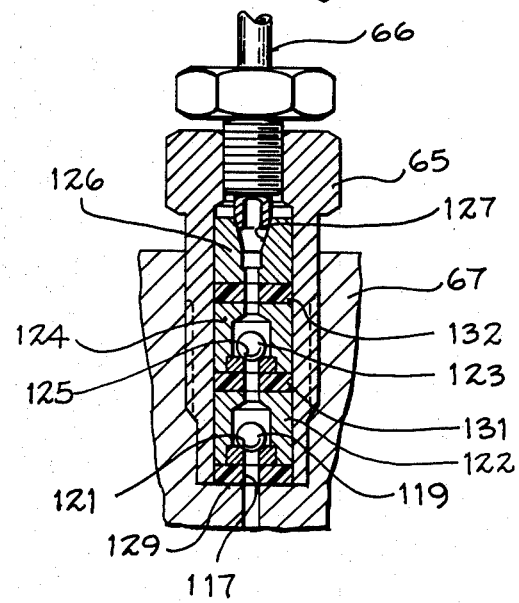
FIG_17
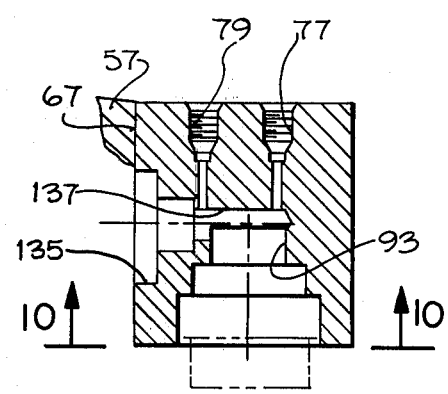
FIG_10
FIG_9

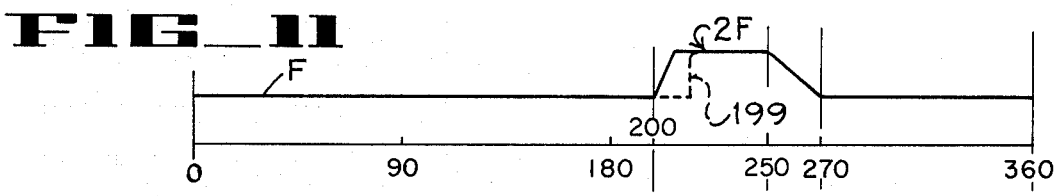
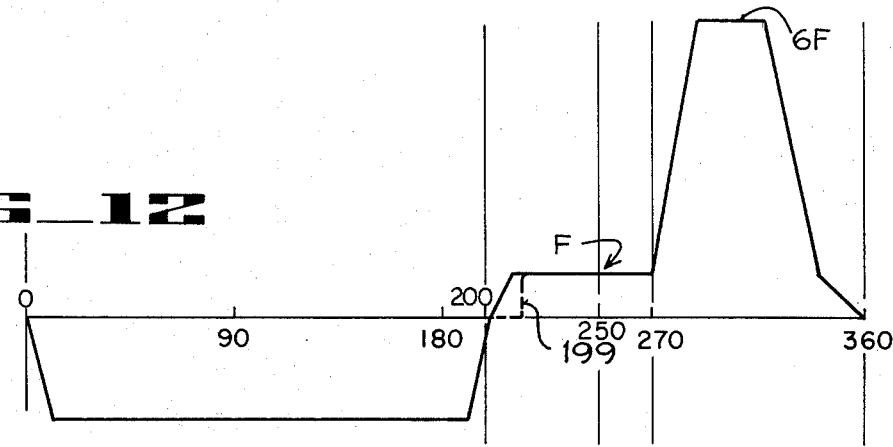
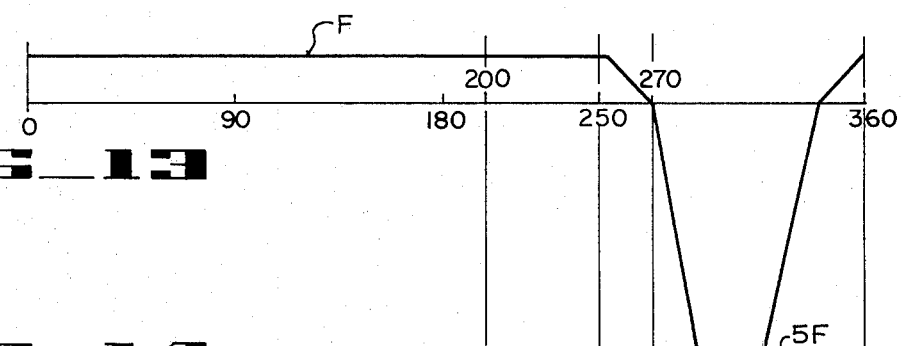
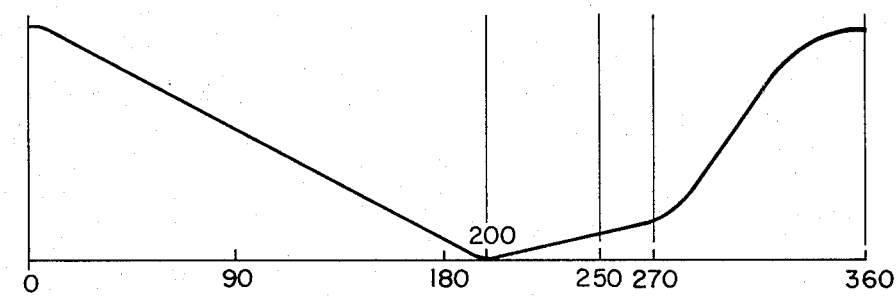
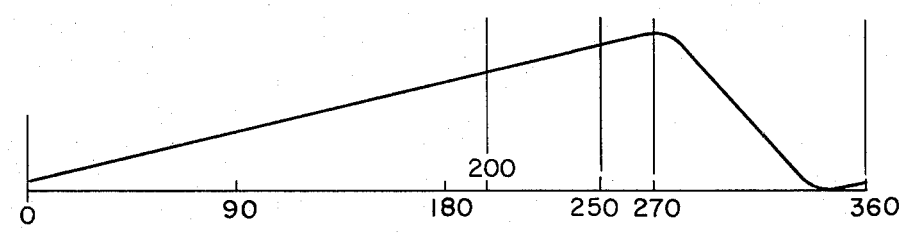

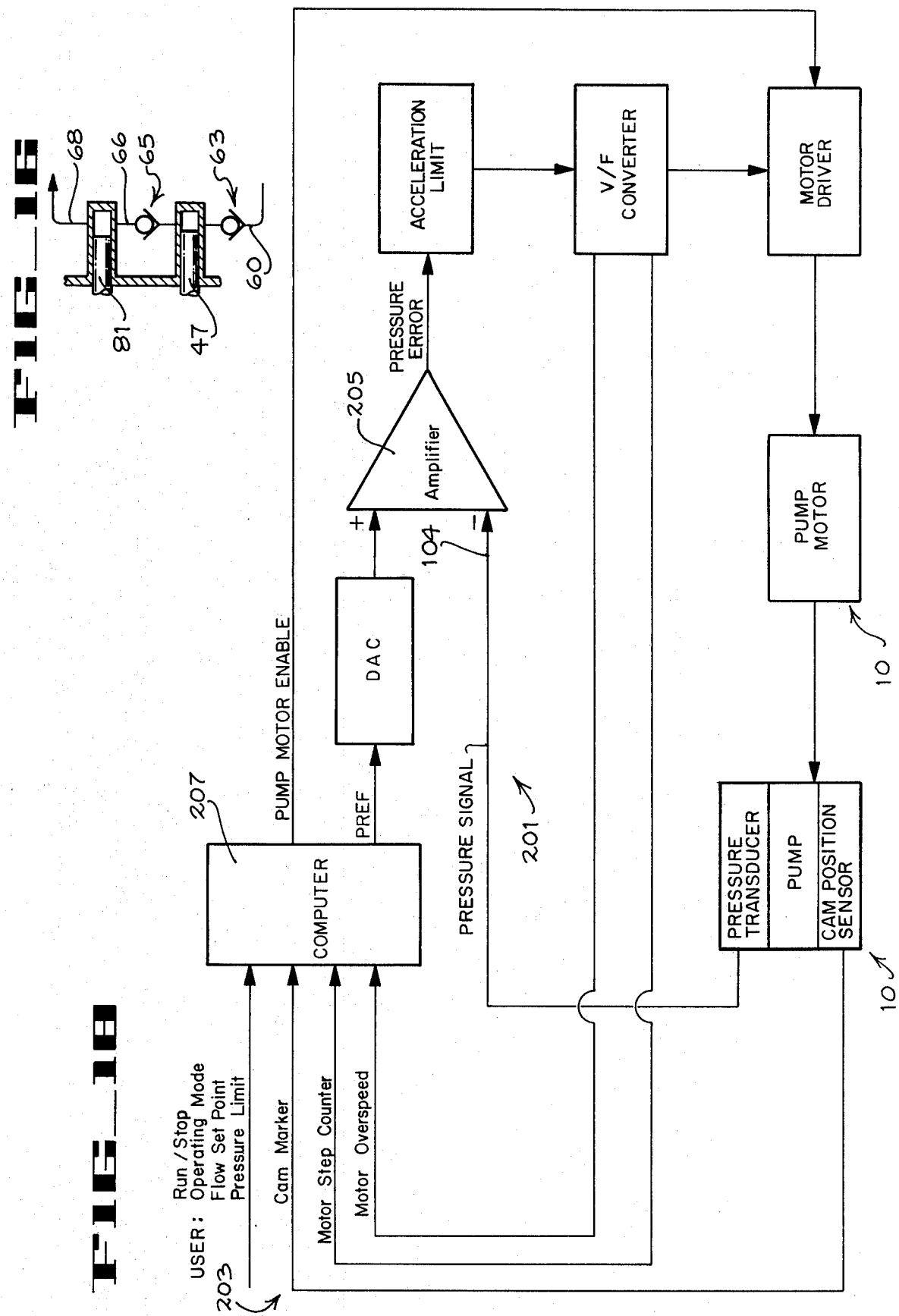

DUAL PISTON PUMP

BACKGROUND OF THE INVENTION

This invention relates to a pump of the kind used for producing a smooth and continuous outflow of liquid at relatively high pressure.

This invention has particular application to a pump used for liquid chromatography.

In liquid chromatography the performance and data which can be obtained from the column and detector of the liquid chromatograph is dependent upon the characteristics of the flow of liquids supplied. A smooth and continuous flow of liquid at pressures up to 6000 psi is necessary to ensure repeatability and accuracy of chromatographic data.

When the liquid supplied to the column and detector is formed as a composition of solvents, performance is also dependent upon accuracy and smoothness of the liquid composition.

The pressurization of the liquid is typically accomplished by piston type pumps. Single piston pumps and multiple piston pumps have been used in the prior art.

Single piston pumps are inherently pulsating type flow devices. Single piston pumps therefore present problems in achieving both of the above requirements.

The single piston pumps have required auxiliary devices to smooth out the pulsating flow. Hydraulic capacitor (such as bourdon tubes) type devices have been used with single piston pumps to try to smooth out the flow, but these type devices do not produce the essentially pulseless flow desired.

Because the single piston pump has no flow at the beginning of the pump cycle (during its intake stroke), single piston pumps have usually been constructed to provide a very fast intake stroke. This causes poor accuracy of composition when the liquid composition being pressurized is formed by proportioning valves at the inlet of the pump. Using a very short intake stroke for the single piston pump makes timing and actuation of the proportioning valves unnecessarily critical. To get good accuracy of composition forming it is better to have a suction stroke which is of sufficient duration so that any inaccuracies in the timing of the solvent proportioning valves do not become appreciable. This long intake stroke which is desired for accuracy of composition forming conflicts with the short intake stroke which is desired for minimizing pulsations in the outflow of a single piston pump.

The prior art has also used a two piston pump with the pistons flow connected in parallel to try to avoid the pressure pulsations in the outflow. In one prior art pump construction of this kind, the two pistons have been driven by one cam with the two pistons located on opposite sides of the drive came so as to be driven 180° out of phase with one another. These dual piston pumps provide almost pulseless flow but are more complex than single piston pumps. They require an inlet valve and an outlet valve for each piston.

This parallel piston pump arrangement of the prior art can present problems in obtaining pulseless flow because of compressibility of the liquid being pumped. In looking at the outflow from the pump there is a decrease in flow at the start of the expulsion stroke of each piston, and the amount of the decrease is largely a function of the compressibility of the liquid and the pressure.

One prior art technique which was developed to compensate for this decrease in flow at the start of the expulsion stroke was to speed up the pump motor in response to the dip. Mechanical inertia, friction, and hydraulic loading are factors which limit the achievable motor acceleration. Increasing the speed of a stepper motor rapidly enough under these conditions at the beginning of the displacement stroke can be a problem.

This parallel piston pump arrangement can also present problems in obtaining accuracy and smoothness of composition when the liquid composition is formed by proportioning valves at the inlet of the pump. Because of the parallel flow connection, a change in inlet composition will not be accomplished smoothly at the pump outlet. After one piston delivers the new composition, the second piston will also deliver the new composition but this will be preceded by the old composition contained in the flow passage between the second piston and the junction with the flow passage from the first piston.

SUMMARY OF THE INVENTION

It is a primary object of the present invention to produce a smooth and continuous flow of liquid at high pressure.

It is a related object of the present invention to produce the smooth and continuous outflow with a dual piston pump which permits a long, extended suction stroke of sufficient duration to obtain accurate composition forming from an inlet solvent proportioning valve.

It is another related object of the present invention to operate one of the pistons very much like a single piston pump and to operate the other piston as a mechanically driven flow damper to smooth out flow variations from the first piston.

It is another object of the present invention to produce a flow positive pulse, rather than a negative pulse, at a certain point in the cycle of operation of the pump so that a motor control system can slow down the pump (and thereby put less work into the system) to eliminate the pulse at this point rather than being required to speed up the pump to eliminate a negative pulse.

It is another object of the present invention to construct a dual piston pump which requires only two check valves.

It is another object of the present invention to improve composition smoothness when using an inlet solvent proportioning valve by flow connecting the dual pistons in series.

It is another object of the present invention to construct a control system for the pump which decouples short term effects from long term effects by responding to short term effects with an analog operated control loop and by responding to long term effects by a microprocessor digitally operated control loop.

A pump constructed in accordance with one embodiment of the present invention has two piston assemblies connected in series.

The first pressure piston assembly includes a pressure piston which has a long inlet stroke and a relatively short and abrupt expulsion stroke.

The second piston assembly includes a damper piston which is driven in cooperation with the movement of the pressure piston to smooth out the outflow from the pressure piston. This smoothing out is accomplished by storing some of the liquid displaced by the expulsion stroke of the pressure piston in the damper piston assembly during the inlet stroke of the damper piston and then delivering the stored pressurized liquid to the outlet of the pump during the suction stroke of the pressure piston.

The outlet from the pressure piston assembly is connected to the inlet to the damper piston assembly with a valve which allows flow in one direction only, which is into the damper piston assembly. The pump outflow is thus the sum of the outflow of the pressure piston assembly and the inflow or outflow of the damper piston assembly.

The pressure piston is driven by a pressure piston drive cam, and the damper piston is driven by a damper piston drive cam. Both drive cams are mounted on a common drive shaft.

The cams are contoured to produce the same amount of outflow of pressurized liquid from the pump at all points in the cycle of rotation of the cam shaft, except for a short interval at the beginning of the expulsion stroke of the pressure piston. Rotation of the cam shaft, during this short interval, at the same speed as the speed at which the cam shaft is rotated during the rest of the cycle, produces a positive outflow pulse at the beginning of the expulsion stroke of the pressure piston.

This positive pulse compensates for compressibility of the liquid. It permits a stepper motor drive to be slowed down in response to a sensing of increased flow at this point in the cycle of operation.

The control system for controlling the speed of rotation of the motor driving the pump has two control loops. One control loop uses a microprocessor to compute the pressure reference for longer term effects. The other control loop responds to short term effects with an analog system. It provides rapid response during the short interval time (at the start of the inlet stroke of the pressure piston) in which a positive pulse of flow would be produced if the speed of rotation of the drive motor were not properly slowed down from the rate of rotation produced during the rest of the cycle.

The system of the present invention utilizes only two check valve assemblies. It eliminates two of the check valve assemblies required in prior art parallel dual piston pumps. This has the advantage of eliminating two of the more unreliable components in liquid chromatography pumping systems, and it also reduces the cost of the system.

The series connected dual piston pump of the present invention enables the length of the suction stroke to be tailored to the particular liquid chromatography application and solvent compositions for which the pump is to be used.

Since the pump of the present invention does not require a rapid suction stroke, it eliminates or minimizes many of the problems previously associated with the rapid intake strokes of single piston pumps, such as, pressure fluctuations, cavitation of high vapor pressure solvents, bubbling of dissolved gases, and incomplete filling of the piston chamber with high viscosity solvents.

The long inlet stroke of the pump of the present invention, as noted above, improves accuracy of low pressure composition forming at the inlet. Timing accuracies of mixing valves become less critical.

The series connected dual piston pump of the present invention does not tend to introduce unwanted composition variations with a multicomponent solvent as do pumps with parallel connected pistons. Because both pistons are in line, the pump of the present invention provides no place for storage of the previous composition during change to a new solvent composition.

Dual piston pump apparatus and methods which incorporate the structure and techniques described above and which are effective to function as described above constitute specific objects of this invention.

Other and further objects of the present invention will be apparent from the following description and claims and are illustrated in the accompanying drawings which, by way of illustration, show preferred embodiments of the present invention and the principles thereof and what are now considered to be the best modes contemplated for applying these principles. Other embodiments of the invention embodying the same or equivalent principles may be used, and structural changes may be made as desired by those skilled in the art without departing from the present invention and the purview of the appended claims.

BRIEF DESCRIPTION OF THE DRAWINGS

FIG. 1 is an elevation view in cross section through the longitudinal axis of a dual piston pump constructed in accordance with one embodiment of the present invention. FIG. 1 is taken along the line and in the direction indicated by the arrows 1—1 in FIG. 2.

FIG. 2 is an elevation view in cross section of the pump shown in FIG. 1 and is taken along the line and in the direction indicated by the arrows 2—2 in FIG. 1, FIG. 4 and FIG. 7.

FIG. 3 is a fragmentary view in cross section of a part of the cylinder block of the pump. FIG. 3 is taken along the line and in the direction indicated by the arrows 3—3 in FIG. 2 and FIG. 4.

FIG. 4 is a top plan view of the pump shown in FIGS. 1 and 2 and is taken along the line and in the direction indicated by the arrows 4—4 in FIG. 2.

FIG. 5 is a fragmentary view showing details of the mounting of a pressure transducer for the pump shown in FIGS. 1 and 2.

FIG. 6 is a fragmentary view taken along the line and in the direction indicated by the arrows 6—6 in FIG. 4. FIG. 6 shows details of the bores for the damper piston and the pressure piston.

FIG. 7 is an elevation view taken along the line and in the direction indicated by the arrows 7—7 in FIG. 2 and FIG. 4.

FIG. 8 is an isometric view of the pump shown in FIGS. 1 and 2.

FIG. 9 is a fragmentary view taken along the line and in the direction indicated by the arrows 9—9 in FIG. 4 and shows details of the association of the inlet and outlet openings for the damper piston with the passage 93 associated with the pressure transducer shown in FIG. 5.

FIG. 10 is a fragmentary view (taken along the line and in the direction indicated by the arrows 10—10 in FIG. 2 and FIG. 5) and shows details of the structure on the underside of the cylinder block 67 for mounting the pressure transducer of FIG. 5.

FIG. 11 is a graph showing outflow per degree cam shaft rotation plotted against cam shaft rotation for the pump.

FIG. 12 is a graph of the independent pressure piston displacement per degree cam shaft rotation plotted against cam shaft rotation.

FIG. 13 is a graph of the independent damper piston displacement per degree cam shaft rotation plotted against cam shaft rotation.

FIGS. 12 and 13 are derived from mathematically differentiating with respect to cam shaft rotation the displacements shown in FIGS. 14 and 15.

FIG. 14 is a graph of displacement of the pressure piston plotted against cam shaft rotation.

FIG. 15 is a graph of displacement of the damper piston plotted against cam shaft rotation.

FIG. 16 is a schematic, diagrammatic view showing the flow path through the pressure piston and the damper piston.

FIG. 17 is a fragmentary, cross section view through the outlet check valve assembly for the pressure piston. FIG. 17 is taken along the line and in the direction indicated by the arrows 17—17 in FIG. 8.

FIG. 18 is a block diagram of a control loop for controlling the speed of rotation of the pump of FIGS. 1 and 2.

DESCRIPTION OF THE PREFERRED EMBODIMENTS

A dual piston pump constructed in accordance with one embodiment of the present invention is indicated generally by the reference numeral 10 in FIGS. 1, 2, 4, 7, 8 and 18 of the drawings.

As shown in FIG. 16 the pump 10 of the present invention has two pistons 47 and 81 flow connected in series between an inlet conduit 60 and an outlet conduit 68. The piston 47 is a pressure piston, and the piston 81 is a damper piston.

As will be described in more detail below with particular reference to FIGS. 11–15 (which graphically illustrate the mode of operation of the pump 10), the flow connection of the two pistons 47 and 81 in series and the related drive arrangement for these two pistons produce a smooth and continuous flow of the liquid being pumped. The pump 10 is effective to maintain substantially pulseless flow even at high pressures, where compressibility of the liquid can present the problem of avoiding a drop in outflow at the start of a compression stroke.

FIGS. 2–10 and FIG. 17 show details of construction of the pump 10, and the structure shown in these figures will now be described.

As illustrated in FIG. 8, the pump 10 comprises a pump housing 57 and a cylinder block 67.

A drive motor 11 drives the pump. The liquid to be pressurized is conducted to the pump by an inlet conduit 60, and the pressurized fluid is conducted from the pump by an outlet conduit 68.

In a particular embodiment of the present invention, the pump 10 is used for pressurizing solvents used for liquid chromatography; and, as illustrated in FIG. 8, a solvent selecting valve 115 is associated with the inlet conduit 60. The valve 115 shown in FIG. 8 is a ternary proportioning valve like that shown in U.S. Pat. No. 4,128,476 to Rock and U.S. Pat. No. 4,137,011 to Rock (both assigned to the same assignee as the assignee of this application).

FIG. 8 also shows a retaining ring 87 which holds a pressure transducer (shown and described in more detail below with reference to FIGS. 5, 9 and 10) in the underside of the cylinder block 67. A conduit 104 conducts the signal from the pressure transducer to one input of an amplifier in a control loop for controlling pump speed under certain conditions of operation, as will be described in greater detail below with reference to FIG. 18.

With reference now to FIG. 1, the drive motor 11 drives the cam shaft 21 of the pump 10 through speed reduction gears 13, 15, 17 and 19.

The cam shaft 21 is mounted for rotation within bearings 23 and 25.

Two cams are mounted on the cam shaft 21 for rotation with the cam shaft 21. These are the cams 27 and 29 shown in FIG. 1. The cams are separated by a spacer 31. Each cam drives a related rocker arm 33.

As illustrated in FIG. 2 and FIG. 7, each rocker arm 33 is mounted for rotation on a bearing 35 about a pivot shaft 36. Each of the cams 27 and 29 engages a related cam follower bearing 37 mounted at the lower end of a related rocker arm 33. An upper cam follower bearing 39, mounted at the upper end of the rocker arm 33, engages a push rod of a piston assembly.

As illustrated in FIG. 2 the cam follower bearing 39 engages a push rod 41 for a piston assembly 43 for the pressure piston 47.

While not illustrated in the drawings, the upper cam follower 39 of the rocker arm 33 associated with the cam 29 engages a similar push rod for the piston assembly containing the damper piston 81.

This rocker arm drive arrangement minimizes side thrust on the push rods. The rocker arm arrangement folds the power train to provide for more compact packaging.

With continued reference to FIG. 2, the push rod 41 pushes the piston assembly 43. The piston assembly 43 comprises a piston head 45 and the pressure piston 47.

A return spring 49 works against the piston head 45.

A seal 51 and a piston guide 53 encircle the pressure piston 47 within a bore 95 in the cylinder block 67.

A seal retainer 55 holds the seal 51 and piston guide 53 in place. The seal retainer 55 fits within a bore 131 in the cylinder block 67.

The piston 47 reciprocates within a bore 133 in the cylinder block 67.

With reference to FIG. 4, the line of action for the pressure piston 47 is indicated at 69 and the line of action for the damper piston 81 is indicated at 71.

The check valves assemblies 63 and 65 (see FIG. 16) are associated with the pressure piston 47 in the cylinder block 67 as shown in FIG. 2.

The center line for the inlet passage of the inlet check valve assembly 63 is indicated at 59 in FIG. 2, and the center line for the outlet passage of the outlet check valve assembly 65 is indicated at 61 in FIG. 2.

The inlet check valve assembly 63 fits within a threaded opening 75.

The outlet check valve assembly 65 fits within a threaded opening 73 in the cylinder block 67.

FIG. 17 shows details of construction of the outlet check valve assembly 65. As shown in FIG. 17, the valve assembly 65 comprises an inlet 117, a ball 119 which seats on a seat 121 a seat holder 122 and a second ball 123 which seats on a seat 125 and a seat holder 124. The valve assembly 65 has three plastic sealing disks 129, 131 and 132. The valve assembly 65 has an outlet 127 in a fitting 126 which receives a tube and the fitting 66 and applies compressive force to the sealing disks 129, 131 and 132.

The construction of the inlet check valve assembly 63 is the same as that of the outlet check valve assembly 65 except that the parts 119, 121, 122, 123, 124 and 125 are inverted.

Each of the check valve assemblies 63 and 65 has two balls and two seats in series for reliability.

With reference to FIG. 4 there are two ports in the cylinder block 67 associated with the damper piston 81. These are an inlet port 77 and an outlet port 79.

As illustrated in FIGS. 8 and 16, the inlet port 77 is connected by the tubing 66 to the outlet check valve assembly 65 associated with the pressure piston 47, and the outlet port 79 is connected to the tubing 68 which conducts the pressurized fluid to the liquid chromatograph, or other apparatus for which the fluid is pressurized by the pump.

With reference to FIGS. 3, 5, 9 and 10, the umderside of the cylinder block 67 has a bore 103 and a counterbore 83 for receiving a pressure transducer 82. The upper end 101 of the pressure tranducer 82 fits in the bore 103 and seats on a small flat seal 91. A central, flanged portion of the pressure tranducer 82 fits within the counter-bore 83, and the retaining ring 87 has a bore 107 which fits over a lower end 105 of the pressure transducer 82 to hold the pressure transducer against the seal 91 by means of cap screws 89.

A chamber 93 within the cylinder block communicates with both of the ports 77 and 79 and also with the bore 137 in which damper piston 81 reciprocates.

The bore 139 shown in FIG. 5 corresponds to the bore 95 for the pressure piston and receives the seal and the piston guide (not illustrated in the drawings) for the damper piston 81.

FIG. 6 shows the bore 111 in the pump housing 57 for receiving the piston assembly 43.

As also illustrated in FIG. 6 the pump housing 57 has a similar bore 113 for receiving the piston assembly for the damper piston 81.

Threaded holes 115 and 117 are formed in the pump housing 57 (as illustrated in FIG. 6) for attaching the cylinder block 67 to the pump housing 57.

As best shown in FIGS. 2 and 4, the upper part of the pump housing 57 has an opening 119 which facilitates inspection of the pistons and the springs of the piston assemblies.

As illustrated in FIGS. 1, 2 and 7, a tab 121 is attached to the cam shaft 21 for rotation with the cam shaft. The tab 121 interrupts a light beam path 125 to a photodetector 123 on each revolution of the cam shaft 21 and provides a signal for the control system call "cam marker" in FIG. 18.

The operation of the dual piston pump 10 will now be described with reference to FIGS. 11–15.

Starting with FIG. 14, the high point of the cam 27 for the pressure piston 47 is selected as the zero degree position on the cam and on the plot of the cam shaft rotation for FIG. 14. The zero degree position is therefore the point of maximum displacement of the pressure piston 47. As the cam shaft 21 rotates, the pressure piston 47 retracts and commences its suction or intake stroke. The suction stroke is a long suction stroke which is desired to provide better accuracy on composition forming (when two or more liquids are combined to form the composition of the liquid to be pressurized). In FIG. 14 the suction stroke is shown as continuing from zero degrees to 200 degrees of rotation of the cam shaft 21.

From the 200° point, the piston 47 starts its pressurization and expulsion stroke. The cam 27 is contoured to increase the displacement of the piston 47 relatively slowly up to 270° and then to increase the displacement rapidly up to the maximum displacement at 360°. At that point we are at the same piston displacement as at 0°, and this represents one complete stroke or cam cycle for the pressure piston 47.

A primary function of the damper piston 81 is to smooth out the rather abrupt flow expulsion of the pressure piston 47.

FIG. 15 shows the displacement of the damper piston 81 versus cam shaft rotation. As can be seen from FIG. 15, the cam 29 is contoured to cause the piston 81 to have a relatively slow displacement from 340° through 0° and up to 270°.

The displacement reverses rapidly from 270° to 340°.

There is a required relationship between the displacements of the two pistons 47 and 81, and the required relationship is necessary to produce the required total flow.

Looking now at FIG. 12, the flow velocity for the pressure piston 47 is plotted against cam shaft rotation. The flow velocity is defined to mean the change in displacement per degree of cam shaft rotation. The velocity curve of FIG. 12 is a mathematical derivitive with respect to cam degrees of the piston displacement curve of FIG. 14.

Similarly, the flow velocity curve of FIG. 13 is a mathematical derivative of the piston displacement curve of FIG. 15 for the damper piston.

Summation of the pressure and damper piston flow velocities is accomplished by flow connecting the pistons in series. A check valve at the inlet and a check valve at the outlet of the pressure piston directs flow in one direction only.

FIG. 11 shows the outflow of the pump into the tubing 68 and is the summation of the flows shown in FIGS. 12 and 13. At zero cam degrees the flow output is steady at the level F. The flow output remains steady in a constant value up through 200°. At 200° the outflow increases to approximately double the previous flow and remains at the level 2F to 250°. At 250° the outflow decreases to the original flow at 270°.

Summation of the flow velocities of FIGS. 12 and 13 is accomplished in the following manner. From zero cam degrees to 200° the pressurization piston moves through its inlet stroke. Liquid enters the bore 133 through the inlet check valve. Previously pressurized and expelled liquid is prevented from flowing back into the bore 133 by the outlet check valve.

From zero to 200 cam degrees, the damper piston moves through a portion of its expulsion stroke providing the constant flow F shown in FIG. 11.

From 200° to 270° the pressurization piston starts its pressurization and expulsion stroke and continues the expulsion stroke at a rate of F. The damper piston is still expelling liquid at a rate F so that the total damper outflow rises to 2F as shown in FIG. 11.

At 250° the damper piston starts decreasing its flow.

At 270° the damper piston stops expelling liquid and the pump outflow drops to F.

From 270° to 340° the pressure piston expulsion rises to a level of approximately 6F and then falls to F. The damper piston starts its storage stroke rising to a negative flow level of approximately 5F and then returning to zero flow. The summation of the pressure piston expulsion and the damper piston storage results in a pump outflow of F in this region.

From 340° to 360° the pressure piston expulsion falls from F to zero and the damper piston expulsion rises from zero to F and in summation results in a pump outflow of F.

The reason for producing the excess flow 2F is to accommodate compressibility of fluids at high pressures. At high pressures, such as the 6000 psi that the pump of the present invention can be used for, appreciable compressibility of liquids being pumped is encountered. Because of this fact the pressure piston 47 has to travel a certain number of cam degrees before it can actually displace a fluid against this pressure. This effect is illustrated in FIG. 12 by the dashed line 199. This effect is also illustrated in FIG. 11 by the dashed line 199.

As noted above, the amount of excess flow (which would be produced by a constant speed of rotation of the cam shaft 121) is designed to accommodate the compressibility of some of the more compressible fluids at the higher pressures encountered.

At lower pressures in order to eliminate this double flow condition that we see in FIG. 11, that is, in order to produce a smooth flow during this period of time, the pump motor is slowed down by a pump control system shown in FIG. 18.

It is an important feature of the present invention that a region of double flow has been chosen to handle compressibility rather than a region of depleted flow. Control systems using stepper motors can behave much more rapidly in slowing the motor down than in speeding it up.

Looking at FIG. 11, the pump is driven at a uniform speed up to 200°. Between 200° and 270° the pump is slowed down rapidly as required to eliminate the rapid rise from F to 2F shown as 199.

When it is time to speed the motor back up in the area from 250° to 270°, the increase in speed of the motor is prescribed by the slope of the outflow in this region. The pressure piston and damper piston cam profiles prescribe this slope and are designed to provide a relatively slow increase in motor speed.

It should also be noted that the effect of the area of double flow on outflow pressure in the tube 68 decreases with increasing levels of pressure of the fluid being pumped. Thus, when the pump is run at constant r.p.m. (without any pressure feedback control) variations in the output pressure due to the double flow area 2F become quite small at about 3000 psi and are very minimal at about 5000 psi.

FIG. 18 is a block diagram view illustrating a control arrangement for regulating the speed of rotation of the cam shaft 21 of the pump.

In FIG. 18 PREF is the pressure reference signal which is provided by the computer.

The DAC is a digital to analog converter that changes the digital computer output to an analog signal appropriate for the amplifier.

The acceleration limit constrains the pressure error signal to keep the error signal within acceleration and deceleration limits which are compatible with the capability of the drive for the pump. In one embodiment of the invention, the pump motor is a stepper motor. A stepper motor cannot always be accelerated at any rate required by a pressure error signal. For example, if the rate is too high, the stepper motor loses synchronism with the driver power frequency, and the motor stalls. The acceleration limit of the FIG. 18 control prescribes a slow acceleration rate for pressure errors requiring more than approximately a 2 to 1 speed change, a fast acceleration rate for pressure errors requiring less than an approximately 2 to 1 speed change, and an even faster deceleration rate independent of the pressure error signal.

The V/F converter converts the pressure error signal (as limited by the acceleration limit) into a frequency proportional to the pressure error.

The motor driver converts a frequency signal into power output to drive the pump motor at a speed proportional to the frequency.

The pump motor drives the pump. The pump contains the pressure transducer and the cam position sensor, and these components provide control signals to the amplifier and to the computer.

The cam position sensor provides a signal to identify the start of the cam cycle. From this start point, the inlet stroke and solvent proportioning and the flow pulse region are determined in the computer by motor step counting relative to this start point.

The computer, upon input commands of start and flow set point, cyclicly computes and supplies to the analog control loop a stepwise increasing pressure reference. This pressure reference continues to increase until the motor step input signal is comparable to the flow set point.

The control system shown in FIG. 18 is used to further smooth out pressure pulses in the outflow conduit 68.

The control system shown in FIG. 18 comprises basically two control loops for the pump.

One loop is an inner control loop 201 which is an analog control loop that uses the signal from the pressure transducer 82.

The pressure transducer signal is supplied to an amplifier 201 which when compared to a pressure reference signal (PREF in FIG. 18) then produces a control signal that calls for more pump speed or less pump speed (as required) to maintain the constant pressure. In a restrictive flow system, with constant fluid properties, pressure is proportional to flow and thus flow is controlled.

The outer control loop 203 observes the time for a specified number of motor steps, the pump speed. That signal goes into a computer 207 to algorithms that compare this against the required flow rate. If, for example, because of a viscosity change in the solvent, the pump has to slow down to maintain constant pressure, the computer 207 calculates the change of speed needed to keep the flow the same. In such a case more pressure would be required, so the computer 207 calculates and produces the appropriate increased pressure reference signal that goes to the amplifier 205. The computer 207 in the outer control loop is assigned the job of computing a pressure reference based on the actual pump speed compared to the desired speed.

The control system shown in FIG. 18 is thus a hybrid control system comprising an inner loop operating analog fashion and an outer loop which operates digitally and uses the pump speed to compute and reset the pressure reference for the inner loop.

The pump motor driven is under the control of the analog loop 201 at all times. The digital loop 23 resets the pressure reference signal under certain conditions of operation.

The analog control loop 201 provides a faster and more authoritative response than the digital computer 207 which is actually too slow to handle the pressure correction directly.

There are a number of conditions that can make it necessary for the computer to change the pressure reference. One condition is a viscosity change, as noted above. Other conditions that can cause changes in flow at constant pressure include, a change in the composition of the solvent, a leaky check valve, a piece of dirt that gets into a check valve. Temperature effects on the restrictions in the system can also cause changes in flow.

During most of the cam shaft rotation each cam degree is going to have an equal amount of flow. It should be noted that motor steps are proportioned to cam degrees because of rotational correspondence through the gears. There are certain areas, for example, where the double flow occurs, that the counting of motor steps is to be avoided. In this compressibility area the flow output is not proportional to motor steps. The cam marker 121 (see FIG. 1 and FIG. 2) indicates to the computer 207 where this area is. In this area the digital loop suspends its operation.

When the cam shaft rotation leaves the non proportional area, the computer resumes the motor step counting and recomputation of the pressure reference.

The computer 207 maintains constant pressure reference to the amplifier 205 during the blanked out portion of the stroke. At other times, outside the compressibility range, the computer varies the pressure reference signal to the amplifier 205 in response to the inputs shown in FIG. 18.

In a particular embodiment of the invention, the cam cycle is divided into ten segments. Each segment has an equal number of degrees corresponding to an equal number of motor steps. The computer computes a new pressure reference for each segment, except two of the segments that are blanked out because of the compressibility occurance. During these two blanked out segments the computer does not compute a new pressure reference. It (as noted above) instead maintains the previous pressure reference.

While we have illustrated and described the preferred embodiments of our invention, it is to be understood that these are capable of variation and modification, and we therefore do not wish to be limited to the precise details set forth, but desire to avail ourselves of such changes and alterations as fall within the purview of the following claims.

We claim:
1. A pump for producing a continuous outflow of liquid at relatively high pressure and comprising,
  pressure piston means for pressurizing the liquid,
  said pressure piston means including a pressure piston movable through suction and expulsion strokes,
  damper piston means for storing some of the liquid displaced by the pressure piston during the expulsion stroke of the pressure piston and for delivering the stored pressurized liquid to an outlet of the pump during the suction stroke of the pressure piston,
  said damper piston means including a damper piston movable through storage and expulsion strokes,
  connecting means connecting the pressure piston means and the damper piston means in series with the flow outlet from the pressure piston means connected to the flow inlet to the damper piston means,
  drive means for driving the pressure piston and damper piston in cooperation to produce a continuous outflow of pressurized liquid from the damper piston during all conditions of movement of the pistons,
  said drive means including a rotatable cam shaft, a pressure piston drive cam mounted on the cam shaft, and a damper piston drive cam mounted on the cam shaft,
  the cams being contoured to produce, at a constant speed of rotation of the cam shaft, a constant amount of outflow of pressurized liquid from the damper piston at all points in the cycle of rotation of the cam shaft except for a short interval at the beginning of the expulsion stroke of the pressure piston and an increased amount of outflow during said short interval,
  control means for slowing down the speed of rotation of the cam shaft during said short interval to produce the same amount of outflow as produced during the rest of the cycle of rotation of the cam shaft,
  sensing means for sensing the increase of outflow from the damper piston during said short interval and for supplying a feedback control signal to the control means, and
  wherein the control means include a first digitally operated control loop which controls the speed of rotation of the cam shaft except during said short interval and wherein the control means include an analog operated control loop which controls the speed of rotation of the cam shaft during said short interval at the beginning of the expulsion stroke of the pressure piston.

2. A pump for producing a continuous outflow of liquid at relatively high pressure and comprising,
  pressure piston means for pressurizing the liquid,
  said pressure piston means including a pressure piston movable through suction and expulsion strokes,
  damper piston means for storing some of the liquid displaced by the pressure piston during the expulsion stroke of the pressure piston and for delivering the stored pressurized liquid to an outlet of the pump during the suction stroke of the pressure piston,
  said damper piston means including a damper piston movable through storage and expulsion strokes,
  connecting means connecting the pressure piston means and the damper piston means in series with the flow outlet from the pressure piston means connected to the flow inlet to the damper piston means, and drive means for driving the pressure piston and damper piston in cooperation to produce a continuous outflow of pressurized liquid from the damper piston during all conditions of movement of the pistons,
  said drive means including a rotatable cam shaft, a pressure piston drive cam mounted on the cam shaft, and a damper piston drive cam mounted on the cam shaft, and
  wherein the cams are contoured to produce, at a constant speed of rotation of the cam shaft, a constant amount of outflow of pressurized liquid from the damper piston at all points in the cycle of rotation of the cam shaft except for a short interval at the beginning of the expulsion stroke of the pressure piston and an increased amount of outflow during said short interval to compensate for the compressibility of liquids at high pressure by producing a flow positive pulse and to permit a motor control system to slow down the pump to maintain a smooth flow rather than requiring a motor control system to speed up the pump to eliminate a negative pulse resulting from the compressibility of the liquid.

3. The invention defined in claim 2 including control means for slowing down the speed of rotation of the cam shaft during said short interval to produce the same amount of outflow as produced during the rest of the cycle of rotation of the cam shaft.

4. The invention defined in claim 3 including sensing means for sensing the increase of outflow from the damper piston during said short interval and for supplying a feedback control signal to the control means.

5. The invention defined in claim 2 wherein the pressure piston drive cam is contoured to move the pressure piston through a long inlet stroke, said long inlet stroke being greater than 180° of cam shaft rotation or greater than ½ of the cam shaft rotation cycle time period.

6. The invention defined in claim 2 wherein the outflow from the pump is the sum of the independent flows of the pressure piston and the damper piston.

7. The invention defined in claim 2 wherein the connecting means include first check valve means at the inlet to the pressure piston means and the second check valve means at the outlet from the pressure piston means.

8. The invention defined in claim 2 including solvent proportioning valve means for portioning more than one solvent to the inlet of the pressure piston.

9. The invention defined in claim 2 including control means for regulating the speed of rotation of the cam shaft.

10. The invention defined in claim 9 wherein the control means include two control loops for the drive motor.

11. The invention defined in claim 10 wherein one control loop is an analog loop and including pressure transducer means for sensing the actual outlet pressure of the pump for comparison to a reference pressure signal.

12. The invention defined in claim 11 including comparator means for determining the error between the actual pressure and the reference pressure and including error limiting means for constraining the error signal within acceleration and deceleration limits compatible with the capabilities of the drive means and wherein the rate of deceleration permitted is substantially greater than the rate of acceleration permitted.

13. The invention defined in claim 12 including a digital loop and including pump speed sensing means for sensing the rate and position of rotation of the cam shaft.

14. The invention defined in claim 13 wherein the digital loop includes flow set point means for setting the desired flow output of the pump and comparison means for comparing the rate of rotation of the cam shaft to the desired flow rate and for producing the reference pressure signal.

15. The invention defined in claim 14 including cam position sensing means for identifying a starting point in the cam shaft rotational cycle.

16. A method of producing a continuous flow of liquid at relatively high pressure from a pump and comprising,
connecting a pressure piston assembly and a damper piston assembly in series with the outlet of the pressure piston assembly connected to the inlet of the damper piston assembly,
pressurizing the liquid by moving a pressure piston through a long inlet stroke and a relatively short expulsion stroke, and
smoothing out the outflow from the pressure piston by moving a damper piston in cooperation with the movement of the pressure piston,
said smoothing out step comprising,
storing some of the liquid displaced by the expulsion stroke of the pressure piston in the damper piston assembly during the inlet stroke of the damper piston and
delivering the stored pressurized liquid to the outlet of the pump during the expulsion stroke of the damper piston.

17. The invention defined in claim 16 including driving the pressure piston by a pressure piston drive cam mounted on a rotatable cam shaft and driving the damper piston by a damper piston drive cam mounted on the same cam shaft.

18. The invention defined in claim 17 wherein the cams are contoured to produce, at a constant speed of rotation of the cam shaft, a constant amount of outflow of pressurized liquid from the pump at all points in the cycle of rotation of the cam shaft except for the short interval at the beginning of the expulsion stroke of the pressure piston and an increased outflow during said short interval to compensate for the compressibility of liquids at high pressure by producing a flow positive pulse and to permit a motor control system to slow down the pump to maintain a smooth flow rather than requiring a motor control system to speed up the pump to eliminate a negative pulse resulting from the compressibility of the liquid.

19. The invention defined in claim 18 including slowing down the speed of rotation of the cam shaft during said short interval to produce the same amount of outflow as produced during the rest of the cycle of rotation of the cam shaft.

20. The invention defined in claim 19 including sensing the increased outflow from the damper piston during said short interval and controlling the speed of rotation of the cam shaft in response to the sensed increase in outflow.

21. The invention defined in claim 18 including rotating the drive cams by a motor and controlling the speed of rotation of the motor by a control which includes two control loops.

22. The invention defined in claim 21 wherein one control loop is an analog loop and includes a pressure transducer which senses the actual outlet pressure of the pump for comparison to a reference pressure signal.

23. The invention defined in claim 22 including comparing the actual pressure to the reference pressure signal to determine the error between the actual pressure and the reference pressure signal and constraining the error signal within acceleration and deceleration limts compatible with the capability of the drive motor and wherein the rate of deceleration permitted is substantially greater than the rate of acceleration permitted.

* * * * *